(12) United States Patent
Gangjee

(10) Patent No.: US 6,423,720 B1
(45) Date of Patent: Jul. 23, 2002

(54) PYRIMIDINE COMPOUNDS AND METHODS FOR MAKING AND USING THE SAME

(75) Inventor: Aleem Gangjee, Allison Park, PA (US)

(73) Assignee: Duquesne University of the Holy Ghost, Pittsburgh, PA (US)

(*) Notice: Subject to any disclaimer, the term of this patent is extended or adjusted under 35 U.S.C. 154(b) by 0 days.

(21) Appl. No.: 09/775,064

(22) Filed: Feb. 1, 2001

(51) Int. Cl.$^7$ .................. A61K 31/505; C07D 239/02; C12N 9/08
(52) U.S. Cl. .............. 514/272; 544/319; 544/320; 544/321; 435/192
(58) Field of Search ............ 514/272; 544/319, 544/320, 321; 435/192

(56) References Cited

U.S. PATENT DOCUMENTS 5,739,141 A   4/1998   Varney et al. ............. 514/272
6,140,351 A * 10/2000   Arnaiz et al. ............. 514/336

OTHER PUBLICATIONS

Calas et. al., Eur. J. Med. Chem.—Chim. Ther., (1979), vol. 14(6), pp. 529–537.*
Smal et. al., Chem. Abs., vol. 109, Abs #47847, 1988.*

* cited by examiner

*Primary Examiner*—Mukund J. Shah
*Assistant Examiner*—Tamthom N. Truong
(74) *Attorney, Agent, or Firm*—Debra Z. Anderson; Eckert Seamans Cherin & Mellott, LLC

(57) ABSTRACT

This invention discloses compounds, and pharmaceutically acceptable salts, solvates and prodrugs thereof, useful in therapeutically and/or prophylactically treating patients with an illness. Such illnesses include cancer, and secondary infections caused by *Pneumocystis carinii, Toxoplasma gondii, Mycobacterium tuberculosis*, and *Mycobacterium avium*. The compounds themselves, methods of making these compounds, and methods of using these compounds are all disclosed. The compounds include 5-thiapyrimidines.

13 Claims, 2 Drawing Sheets

PYRIMIDINE COMPOUNDS AND METHODS FOR MAKING AND USING THE SAME

FIELD OF THE INVENTION

This invention relates to pyrimidine compounds and pharmaceutically acceptable salts, solvates and prodrugs thereof. The present compounds have been found useful in resisting and treating infections in immunocompromised patients. These compounds are also useful as antitumor, antibiotic, antimalarial, antifungal, antiprotozoal, antituberculosis and anti*Mycobacterium avium* agents, and can also be used as synergistic agents when used with sulfonamides. Methods of preparing and using these compounds are also provided.

BACKGROUND OF THE INVENTION

Various pyrimidine systems, such as the pyrido pyrimidines, pyrrolo pyrimidines and furo pyrimidines, have been studied due to their involvement in the inhibition of dihydrofolate reductase (DHFR) enzyme activity. Because DHFR reduces dihydrofolate to tetrahydrofolate, inhibition of DHFR deprives the cell of tetrahydrofolate, without which the cell cannot produce 5,10-methylenetetrahydrofolate. 5,10-Methylenetetrahydrofolate is essential for cell growth. The inhibition of DHFR by the compounds of this invention results in the inhibition of DNA synthesis and leads to cell death.

The pyrimidine derivatives disclosed herein also function as thymidylate synthase (TS) inhibitors. TS, along with DHFR, forms part of the system responsible for the synthesis of deoxythymidylate (dTMP) from deoxyuridylate (dUMP). TS catalyzes the sole de novo synthesis of dTMP from dUMP. Inhibition of TS, therefore, deprives the cell of thymidine, which is an essential constituent of DNA.

SUMMARY OF THE INVENTION

The present invention provides pyrimidine compounds, and pharmaceutically acceptable salts, solvates and prodrugs thereof, having the formula (1):

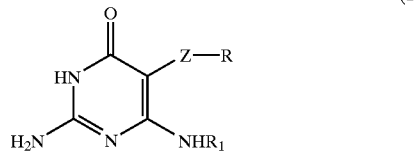

(1)

wherein R is an aryl ring or alkylaryl ring optionally substituted with one or more substituents independently selected from $C_{1-6}$ alkyl groups, $C_{2-6}$ alkenyl groups, $C_{2-6}$ alkynyl groups, $C_{1-6}$ alkoxy groups, halogens, nitro groups, aryl groups, $C_{1-6}$ acyl groups, carboxylic acids, carboxylic esters, hydroxyl groups, mercapto groups, polycarbo groups, and p-aroyl-L-glutamate;

wherein Z is S, Se, O, NH, $CH_2$; and wherein $R_1$ is H or a straight, branched or cyclic alkyl group having up to about six carbons optionally substituted with one or more halogen, hydroxyl or amine groups.

The present invention also provides methods of synthesizing compounds having formula (1). Methods for using these compounds in the treatment of various illnesses are also within the scope of the invention.

More specifically, the invention provides a method of using the pyrimidine derivatives of Formula 1 for therapeutic and prophylactic purposes including employing these compounds to resist and treat secondary infections caused by *Pneumocystis carinii, Toxoplasma gondii, Mycobacterium tuberculosis* and *Mycobacterium avium* complex or other organisms in immunocompromised patients. Immunocompromised patients, for example, may be patients with AIDS, or patients undergoing chemotherapy, steroid treatment, and the like; other immunocompromised patients could also be treated according to this invention. In addition, this invention provides methods of using pyrimidine derivatives as antituberculosis, anti*Mycobacterium avium* complex, antibiotic, antimalarial, antifungal and antiprotozoal agents and as synergistic agents with sulfonamides in such patients, although their use in this application may require the use of leucovorin rescue.

This invention also provides methods of using the present pyrimidine derivatives for therapeutic and/or prophylactic purposes as antitumor agents or to otherwise destroy or minimize growth or proliferation of cancerous cells in cancer patients.

It is an aspect of this invention to provide pyrimidine compounds, and pharmaceutically acceptable salts and prodrugs thereof, for substantially inhibiting dihydrofolate reductase enzymes and/or thymidylate synthase enzymes.

It is another aspect of the present invention to provide derivative compounds, and pharmaceutically acceptable salts and prodrugs thereof, having antitumor, antibiotic, antimalarial, antifungal, antiprotozoal, antituberculosis or anti*Mycobacterium avium* activity or synergistic activity with sulfonamides.

It is a further aspect of this invention to provide pyrimidine compounds having activity against secondary infections, such as infections caused by *Pneumocystis carinii, Toxoplasma gondii, Mycobacterium tuberculosis* and *Mycobacterium avium* that occur in immunocompromised patients.

It is another aspect of this invention to provide a method of synthesizing the present pyrimidine compounds and their derivatives.

These and other aspects of the invention will be more fully understood from the drawing and the following description of the invention and the claims appended hereto.

DETAILED DESCRIPTION OF THE INVENTION

Figure 1:
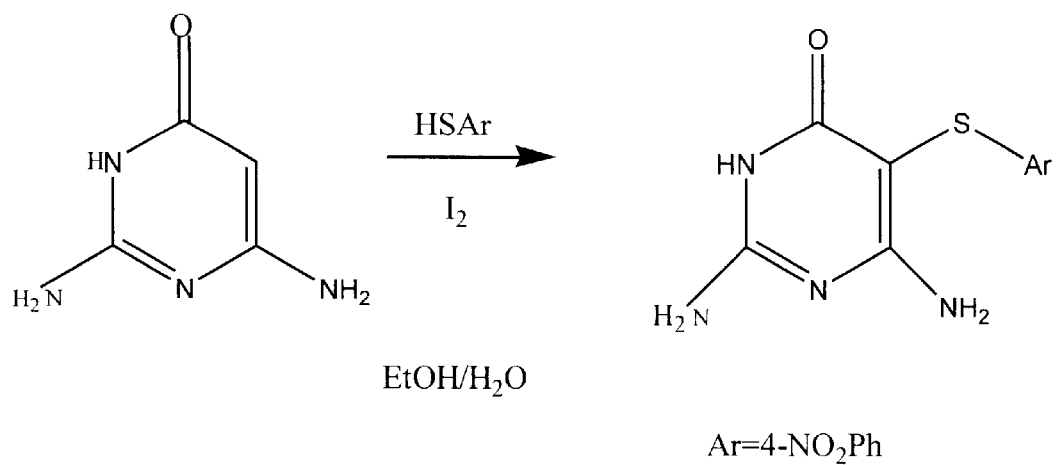
FIG. 1 shows a schematic diagram of the methods for preparing thiapyrimidine compounds having Formula 1.

The present invention is directed to compounds, and pharmaceutically acceptable salts, solvates, and prodrugs thereof, having formula (1):

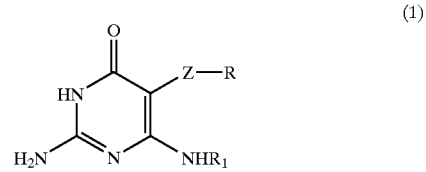

(1)

wherein R is an aryl ring or alkylaryl ring optionally substituted with one or more substituents independently selected from $C_{1-6}$ alkyl groups, $C_{2-6}$ alkenyl groups, $C_{2-6}$ alkynyl groups, $C_{1-6}$ alkoxy groups, halogens, nitro groups, aryl groups, $C_{1-6}$ acyl groups, carboxylic acids, carboxylic esters. hydroxyl groups, mercapto groups, polycarbo groups, and p-aroyl-L-glutamate;

wherein Z is S, Se, O, NH, $CH_2$; and wherein R, is H or a straight, branched or cyclic alkyl group having up to about six carbons optionally substituted with one or more halogen, hydroxyl or amine groups.

"Aryl" groups will be understood as referring to compounds whose molecules have a ring structure, such as the six-carbon ring of benzene, or multiple rings which are either fused or unfused, such as condensed six-carbon rings of other aromatic derivatives. Suitable aryl groups therefore include, for example, phenyl, biphenyl, benzyl, naphthyl, phenanthrene, anthracene groups and aryl oxyaryl groups. Thus, the term "aryl" includes diaryl, triaryl and polyaryl groups, which would have two, three or more rings, respectively. Also included within the term "aryl" are heterocycles, heteroaromatics or heteroaryls, which terms are used interchangeably herein and which will be understood to those skilled in the art as representing closed ring structures having at least one atom in the ring which is not carbon, such as oxygen, nitrogen or sulfur. Examples include but are not limited to pyrimidines, indoles, thiophenes, furans, benzofurans, pyridines, pyrroles, purines, and the like. "Heteroaryls" as used herein also refers to such ring structures that are part of larger ring structures, such as two or three member ring systems, which may be fused or unfused, in which one of the rings is as described above. Thus, heteroaryl can refer to ring systems in which one or more rings contain a heteroatom and one or more rings do not. It will be understood that this list is not meant to be exhaustive, and that any aryl group, as that term is commonly understood in the art, is within the scope of the present invention.

The term "alkylaryl" (or "alkaryl") refers to groups having an alkyl moiety attached to an aryl ring. The alkyl moiety is preferably a straight, branched or cyclic alkyl group having one to about six carbon atoms. This alkyl moiety may also contain oxygen, nitrogen or sulfur atoms, and can therefore be an alkoxy group. The aryl moiety of the alkylaryl group is a substituted or unsubstituted aryl group, as that term is described above.

The aryl and alkylaryl groups are optionally substituted with one or more substituents as listed above. In the case of more than one substituent, the substituents are independently selected. "Alkoxy groups" and "alkyl groups" include straight or branched chains having up to about six members. "Halogen" refers to chlorine, bromine, iodine and fluorine. "Aryl groups" is as described above. When a carboxylic acid is a substituent, it will be appreciated that the moiety represents an acid such as benzoic acid. "Acyl" refers to an organic acid group in which the OH is replaced by some other substituent, and is generally designated as RCO— where R is a $C_{1-6}$ alkyl, $C_{2-6}$ alkenyl, or $C_{2-6}$ alkynyl straight or branched chain group.

As used herein, the term aroyl, such as when used within the term p-aroyl-L-glutamate, refers to heteroaroyl, benzoyl, napthoyl, thiophenoyl, furophenoyl, pyrroyl, and any other "aroyl" as that term would be understood by one skilled in the art. "Aroyl" is generally defined in the art as an aromatic or heteroaromatic compound having a carbonyl moiety. "Glutamate" will be understood as representing both the ester form (glutamate) and the acid form (glutamic acid).

As used herein, the term "pharmaceutically acceptable salts and solvates" include salts or solvates of the present pyrimidine compounds suitable for use in pharmaceutical applications. One skilled in the art would easily be able to determine whether a salt or solvate form of any given compound is suitable for use as a pharmaceutical. Examples of pharmaceutically acceptable salts include but are not limited to, acetate, formate, glucuronate, ethantate, and sulfonate. Other examples include alkaline metal, alkaline earth metal, other non-toxic metals, ammonium and substituted ammonium salts such as the sodium, potassium, lithium, calcium, magnesium, aluminum, zinc, ammonium, trimethyl ammonium, triethyl ammonium, tetrabutyl ammonium, pyridinium and substituted pyridinium salts. "Pharmaceutically acceptable prodrugs" similarly refers to any prodrug formulations of the present compounds. A prodrug will be understood by those skilled in the art as a chemical compound that is converted into an active curative agent by processes within the body. Other formulations comprising the pyrimidine compounds described herein are also within the scope of the present inventions.

It will be understood that "pyrimidine compounds" or "pyrimidine derivatives" as used herein refers collectively to the compounds of Formula 1, pharmaceutically acceptable salts thereof, and prodrugs thereof. In addition, although the compounds of Formula 1 are depicted throughout this description in the 4-oxo form, and are referred to as such throughout this description, the oxo group exists in tautomeric equilibrium with the corresponding 4-hydroxy group and it will be understood that in each case the tautomeric hydroxyl form is also indicated. A compound of the invention may be active per se, or it may be a precursor which is converted in vivo to an active compound. Compounds of the present invention may possess at least one chiral center. Thus, "pyrimidine compounds" include mixtures of diastereomers or enantiomers, as well as diastereomers and enantiomers substantially free of other diastereomers or enantiomers.

The compounds disclosed in the present invention can all be generally described as antifolates that inhibit dihydrofolate reductase (DHFR) enzymes. The DHFR enzymes are needed for normal cell growth because they reduce methylenetetrahydrofolate to tetrahydrofolate. Tetrahydrofolate is a precursor of 5,10-methylenetetrahydrofolate, which is essential for DNA replication and thus cell growth. By inhibiting dihydrofolate reductase, the present compounds consequently inhibit DNA synthesis. Inhibition of DNA synthesis results in cell death.

In addition, the pyrimidine compounds of the present invention inhibit thymidylate synthase (TS). TS, along with DHFR, forms part of the system responsible for the synthesis of deoxythymidylate (dTMP) from deoxyuridylate (dUMP). Inhibition of TS deprives the cell of thymidine, which is an essential component of DNA.

Preferred embodiments of the compounds of Formula 1 are provided in Table 1. For all of these compounds, Z is sulfur and $R_1$ is H.

| Compound | R |
|---|---|
| 167 | 4-chlorophenyl |
| 165 | 1-naphthyl |
| 185 | 4-nitrophenyl |
| 171 | 2-chlorophenyl |
| 184 | 3,5-dichlorophenyl |
| 181 | 3,4-dimethoxyphenyl |
| 175 | 3-methoyphenyl |
| 170 | 4-benzoic acid |

| Compound | R |
|---|---|
| 186 | aryl oxyaryl |
| 176 | 2,6-dichlorophenyl |
| 188 | 2-pyridine |
| 179 | 4-pyridine |
| 198 | 2-methoxyphenyl |
| 199 | 2-(4-phenyl)thiazole |
| 174 | 2-naphthyl |
| 177 | 2,4-dichlorophenyl |
| 169 | 2,5-dimethoxyphenyl |
| 197 | methyl 2-chlorophenyl |
| 180 | methyl 4-chlorophenyl |
| 194 | methyl 4-methylphenyl |
| 196 | methyl 3-methylphenyl |
| 187 | methylphenyl |
| 191 | methyl 3-methyoxyphenyl |
| 190 | methyl 3,4-dichlorophenyl |
| 193 | methyl 2,4-dichlorophenyl |
| 202 | methyl 4-bromophenyl |

The compounds of Formula 1, especially those in Table 1, are potent inhibitors of DHFR and as such have, among other things, excellent antitumor ability and excellent prevention and/or treatment of opportunistic infection ability, including infection caused by, for example, *Pneumocystis carinii, Toxoplasma gondii, Mycobacterium tuberculosis* and *Mycobacterium avium*.

The present invention is also directed to methods for synthesizing compounds of Formula 1 as described above. In one embodiment for preparing thiapyrimidine compounds, the methods generally comprise the steps of combining 2,4-diamino-6-oxopyrimidine with a thiol or mercaptan compound that reflects the substituent to be attached to the five-position of the pyrimidine ring. This compound is referred to herein as the sulfur containing substituent, and is represented by the "Z-R" moiety in formula 1, wherein Z is sulfur and R is as described above. FIG. 1 illustrates the present method for making 2,4-diamino-6-oxo-5-(4' nitrophenylthio) pyrimidine, which is a representative method for making all of the present thiapyrimidine compounds. In the figure, 2,4-diamino-6-oxopyrimidine is reacted with 4-nitrothiophenol. It will be appreciated that 4-nitrothiophenol would be replaced with other compounds depending on the final product desired by the user. 2,4-diamino-6-oxopyrimidine is commercially available from Aldrich Chemical Co. The oxopyrimidine and acidic substituent compound is subjected to a mild reflux. As soon as the reflux starts, iodine is added to the reflux mixture. The reflux step is continued until the sulfur containing substituent reacts with the oxopyrimidine. This period can be as short as 1.5 hours or can take 24 hours or longer. Thin layer chromatography (TLC) can be used to determine the amount of starting material remaining in the reflux mixture. In the embodiment depicted in FIG. 1, the acidic substituent compound is dissolved in an ethanol/water solution comprising a 2:1 volume to volume ratio of ethanol to water. The molar ratio of oxopyrimidine to sulfur containing substituent is in the range of between 1:1 and 1:3. Thus, a stoichiometric excess of the acidic substituent compound can be used. Iodine is added in a molar ratio of between about 1:2 and 1:4 based on the amount of the oxopyrimidine used.

The solution is cooled to room temperature, which causes the solid product to precipitate out. Any means standard in the art can be used to remove the precipitate; filtration is preferred. The residue is then preferably washed with successive ethylacetate, ethanol and ethyl ether washes. This will remove unreacted sulfur containing substituent and other unreacted material, byproducts or contaminants. The washed residue can then be further mixed with, for example, ethanol and refluxed for an additional period of time, such as 2–5 minutes to remove any unreacted sulfur containing substituent that still remains in the mixture. The product that precipitates upon cooling can again be separated from the solution by standard methods, such as filtration. Again, TLC can be used at any stage to determine the presence of unreacted starting material and to confirm the purity of the final product. It is an advantage of the present methods that a pure product results following reflux with ethanol, without the need for additional purification steps.

Figure 2:
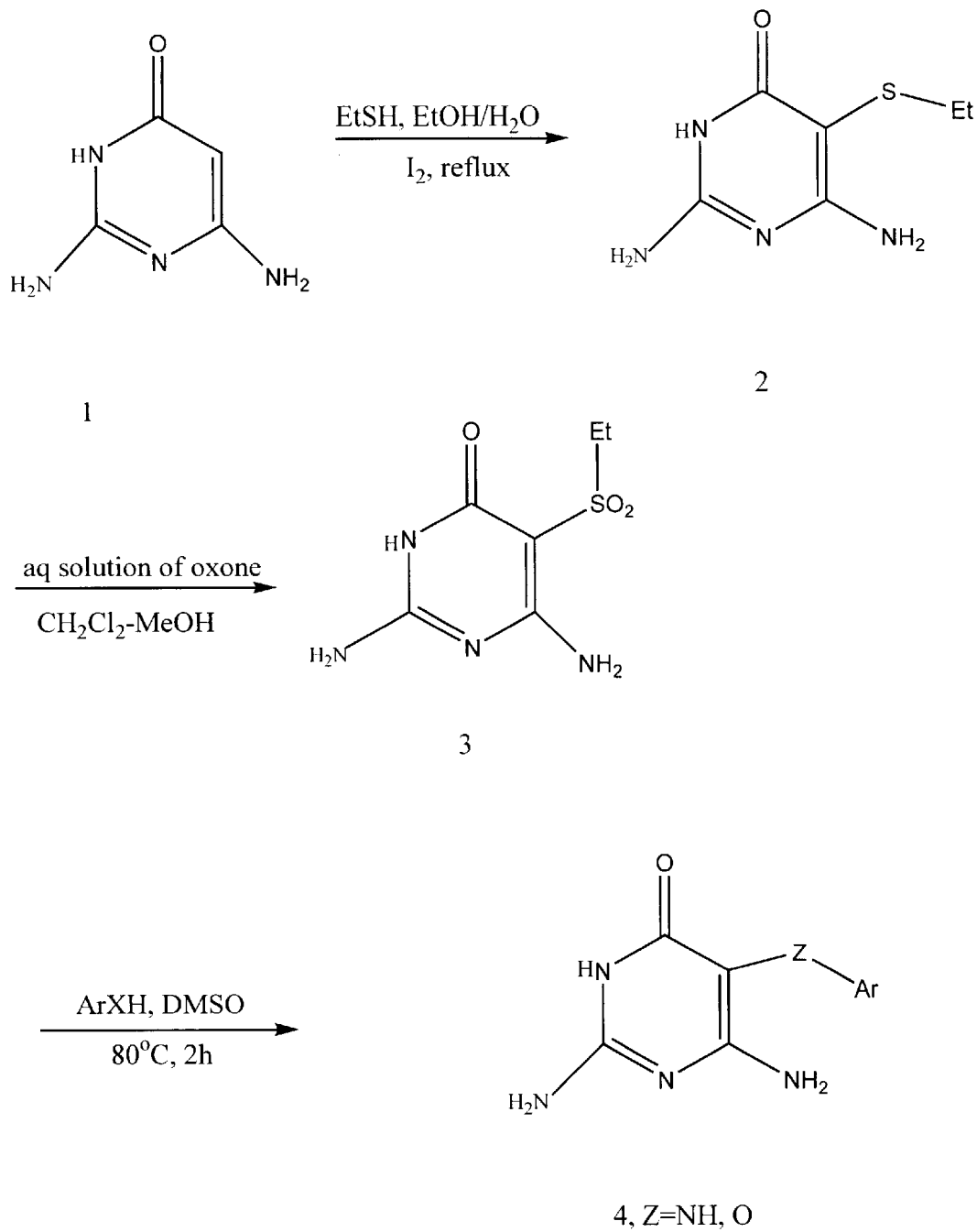
FIG. 2 shows a schematic diagram of the methods for preparing compounds having Formula 1 wherein Z is O or NH.

FIG. 2 illustrates an embodiment of the invention for making compounds of Formula 1 wherein Z is NH or O. Reference numbers refer to those in the figure. In this embodiment, 2,4-diamino-6-oxopyrimidine(1) is refluxed with EtSH in a 2:1 solution of ethanol:water ratio (v/v). Iodine is added cautiously and the mixture refluxed for about two hours, after which the solution is cooled. The precipitate that results upon cooling can be removed, such as by filtration, and washed successively with water, ethyl acetate, ethanol and ethyl ether. Compound 2 results, and is then dissolved in a dichloromethane-methanol solution. An oxone is added to the solution, resulting in compound 3. This compound is then reacted with a compound having the formula ArXH in DMSO to yield compound 4, wherein X is NH or O and Ar is aryl. It will be appreciated that FIG. 2 depicts "R" as an aryl group, but any of the R groups as described above can be used.

Salts, solvates and prodrugs of the compounds of Formula 1 can be made by standard methods well known to those skilled in the art.

The present invention further relates to methods of using the abovedescribed compounds, and pharmaceutically acceptable salts and prodrugs thereof, to treat a patient with an illness. "Treating" and "treatment" are used generically throughout to refer to both therapeutic and prophylactic treating/treatment that is effected by inhibition of DHFR and/or TS in a patient. As used herein, the term "illness" refers to cancer, infection by *Pneumocystis carinii, Toxoplasma gondii, Mycobacterium tuberculosis, Mycobacterium avium,* or other secondary infections arising in immunocompromised patients, such as those with AIDS, and infections caused by bacteria, malaria, fungi or protozoa. "Cancer" refers to any type of cancer including, but not limited to, leukemia, lung cancer, colon cancer, CNS cancer, melanoma, ovarian cancer, renal cancer, prostate cancer, and breast cancer.

A method of treating a patient for an illness according to the present invention comprises administering an effective amount of one or more compounds of Formula 1 to a patient.

As used herein, the term "patient" means members of the animal kingdom including but not limited to human beings.

As used herein, the term "effective amount" refers to that amount of any of the present compounds required to bring about a desired effect in a patient. The desired effect will vary depending on the illness being treated. For example, the desired effect may be reducing tumor size, destroying cancerous cells, or resisting/treating infection caused by organisms such as *Pneumocystis carinii* and *Toxoplasma gondii*. On its most basic level, an effective amount is that amount needed to inhibit DHFR and/or TS. Any amount of inhibition will yield a benefit to a patient and is therefore within the scope of the invention.

It will be appreciated that the effective amount will vary from patient to patient depending on such factors as the illness being treated, the severity of the illness, the size of the patient being treated, the patient's ability to mount an immune response, and the like. The determination of an effective amount for a given patient to is within the skill of one practicing in the art. Typically an effective amount will be determined by evaluating potency in standard ex vivo cellular systems, followed by preclinical and clinical in vivo assessment.

Administration can be by any means known in the art, such as parenterally, orally or topically. The pyrimidine compound can be contained within a suitable pharmaceutical carrier for administration according to the present methods. "Suitable pharmaceutical carrier" refers to any pharmaceutical carrier known in the art that will solubilize the present compounds and will not give rise to compatibility problems and includes any and all solvents, dispersion media, coatings, antibacterial and antifungal agents, isotonic and absorption delaying agents, and the like. The use of such media and agents for pharmaceutical use is well-known in the art. Use of any of these media or agents is contemplated by the present invention, absent comparability problems with the chimeric proteins. Preferred carriers include physiologic saline and 5% dextrose.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of pyrimidine compound to produce the desired effect in association with the pharmaceutical carrier. The specification for the dosage unit forms of the invention are dictated by and directly dependent on the particular compound and the particular effect to be achieved.

EXAMPLES

The following examples are intended to illustrate the invention, and should not be construed as limiting the invention in any way. Standard test procedures familiar to those skilled in the art were used in the examples, such as those procedures described by Gangjee, A., et al., in "5-Arylthio-substituted 2-amino-4-oxo-6-methyl pyrrolo[2,3-d]pyrimidine antifolates as thymidylate synthase inhibitors and antitumor agents", *J. Med. Chem.*, Vol. 38, pp. 4495–4502 (1995); "Effect of bridge region variation on antifolate and antitumor activity of classical 5-substituted 2,4-diamino furo [2,3-d]pyrimidines", *J. Med. Chem.*, Vol. 38, pp. 3798–3805 (1995); and "Novel 2,4-diamino-5-substituted-pyrrolo[2,3-d]pyrimidines As Classical and Non-Classical Antifolate Inhibitors of Dihydrofolate Reductases", *J. Med. Chem.*, Vol. 38, pp. 2158–2165 (Jun. 6, 1995) and references disclosed therein.

Example 1

Synthesis of 2,4-diamino-6-oxo-5-(4'-nitrophenylthio)pyrimidine

A mixture of 2,4-diamino-6-oxopyrimidine (189 mg, 1.50 mmol) and 4-nitrothiophenol (427 mg, 2.20 mmol) in 45 mL EtOH/H$_2$O (2/1, v/v) was refluxed for 10 minutes. To this refluxing solution iodine (0.913 g, 3.60 mmol) was added and reflux continued for two hours. The solution was cooled to room temperature. The precipitate that formed was collected by filtration. The residue was washed with AcOEt, EtOH and Ethyl ether. The light yellow residue was added to 100 mL EtOH and refluxed for three minutes and then cooled to room temperature. The light yellow precipitate was collected by filtration and dried to afford 398.9 mg analytically pure compound (yield 95%).

The following analyses indicate that that product was 2,4-diamino-6-oxo-5-(4'-nitrophenylthio)pyrimidine:

Mp>300° C. (dec.) $^1$HNMR: δ 6.57 (brs, 4H); 7.21 (d, 2H, J=6.93 Hz); 8.09 (d, 2H, J=6.93 Hz); 10.24 (s, 1H). Anal. (C$_{10}$H$_9$N$_5$O$_3$S) C, H, N, S.

| | | | | |
|---|---|---|---|---|
| Calc. | C 43.01 | H 3.25 | N 25.08 | S 11.48 |
| Measured | C 43.04 | H 3.52 | N 24.81 | S 11.80 |

All other compounds of the present invention can be made using this methodology by substituting 4-nitrothiophenol with any compound that will result in the desired substituent being attached to the five position of the pyrimidine. All other parameters such as molar ratios, reflux times, solvents can be readily determined by one skilled in the art following the above guidelines.

Example 2

The compounds described in Table 1 were evaluated as inhibitors of dihydrofolate reductase (DHFR) from *Toxoplasmosis gondii* (Tx) and rat liver (RL). The evaluation of the compounds consisted of determining the IC$_{50}$ values and selectivity ratios of each compound against Tx DHFR and RL DHFR. The IC$_{50}$ value is the concentration of a compound required to inhibit the dihydrofolate reductase activity by 50 percent (%). It will be understood by those skilled in the art that the lower the IC$_{50}$ value the more potent the compound. The selectivity ratio is a measure of the selectivity of a compound for Tx DHFR and is expressed as the IC$_{50}$ value of the DHFR from rat liver (RL) divided by the IC$_{50}$ value of the Tx DHFR. For example, the selectivity ratio of a compound is calculated by the following formula:

$$\frac{IC_{50}RL\ DHFR}{IC_{50}Tx\ DHFR}$$

It will be understood by those skilled in the art that the higher the selectivity ratio, the less toxic the compound is to mammalian dihydrofolate reductase, and thus, less toxic to the patient.

Table 2 sets forth the IC$_{50}$ values for RL DHFR and Tx DHFR and the corresponding selectivity ratios for the compounds tested.

TABLE 2

Inhibitory Concentrations (IC$_{50}$µM) and Selectivity Ratios

| Compound # | RL DHFR[1] | Tx DHFR[1] | Selectivity Ratio: RL DHFR/Tx DHFR |
|---|---|---|---|
| 167 | 19.8 µM | 0.22 µM | 90.0 |
| 165 | 97.2 µM | 0.49 µM | 198.4 |
| 185 | 15 µM | 0.27 µM | 55.6 |
| 171 | 4.7 µM | 0.35 µM | 13.4 |
| 184 | 20.2 µM | 0.27 µM | 74.8 |
| 181 | 19% @ 67 µM | 1.9 µM | >35.2# |
| 175 | 53.4 µM | 0.58 µM | 92.1 |
| 170 | 122 µM | 53.8 µM | 2.3 |
| 186 | 3.4 µM | 0.42 µM | 8.1 |
| 176 | 17.5 µM | 1.7 µM | 10.3 |
| 188 | 117 µM | 4.7 µM | 24.9 |

TABLE 2-continued

Inhibitory Concentrations (IC$_{50}$µM) and Selectivity Ratios

| Compound # | RL DHFR[1] | Tx DHFR[1] | Selectivity Ratio: RL DHFR/Tx DHFR |
|---|---|---|---|
| 179 | 101 µM | 8.5 µM | 11.9 |
| 198 | 263 µM | 5.8 µM | 45.3 |
| 199 | 53 µM | 12.2 µM | 4.3 |
| 174 | 30 µM | 0.35 µM | 85.7 |
| 177 | 2.3 µM | 0.14 µM | 16.4 |
| 169 | 28.5 µM | 0.2 µM | 142.5 |
| 197 | 8.2 µM | 2.2 µM | 3.7 |
| 180 | 26% @ 60 µM | 16.6 µM | >3.16# |
| 194 | 193 µM | 7.6 µM | 25.4 |
| 196 | 3% @ 90 µM | 11.5 µM | >7.18 # |
| 187 | 40.7 µM | 5.3 µM | 7.7 |
| 191 | 66.8 µM | 6.6 µM | 10.1 |
| 190 | 24.2 µM | 1.5 µM | 16.1 |
| 193 | 7 µM | 0.7 µM | 10 |
| 202 | 46.7 µM | 1.9 µM | 24.6 |

The selectivity ratio for these compounds is actually greater than the number given since the RL DHFR value is an IC of <50%.

Compound 170 was also tested against DHFR from *Pneumocystis carinii* (PC). The Pc IC$_{50}$ value was 89.5 µM, and the RL/Pc selectivity ratio was 1.4.

As can be seen from the above table, the compounds are effective in inhibiting DHFR; the compounds have a selectivity ratio>1 and are therefore all more selective for the disease-causing organism (Toxoplasma).

Whereas particular embodiments of this invention have been described above for purposes of illustration, it will be evident to those skilled in the art that numerous variations of the details of the present invention may be made without departing from the invention as defined in the appended claims.

What is claimed is:

1. A compound, and pharmaceutically acceptable salts thereof, having formula (1):

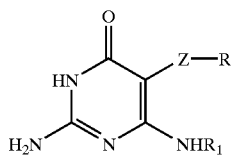

(1)

wherein R is an aryl ring or alkylaryl ring optionally substituted with one or more substituents independently selected from $C_{1-6}$ alkyl groups, $C_{2-6}$ alkenyl groups, $C_{2-6}$ alkynyl groups, $C_{1-6}$ alkoxy groups, halogens, nitro groups, aryl groups, $C_{1-6}$ acyl groups, carboxylic acids, carboxylic esters, hydroxyl groups, mercapto groups, and p-aroyl-L-glutamate;

wherein Z is S, Se, O, NH, $CH_2$; and wherein $R_1$ is H or a straight, branched or cyclic alkyl group having up to about six carbons optionally substituted with one or more halogen, hydroxyl or amine groups; but when Z is S or Se, R is not p-aroyl-L-glutamate; and when $R_1$ is H, and Z is $CH_2$, then R is not a 3,4,5 trimethoxyphenyl group; and when $R_1$ is H, Z=$CH_2$ and R is a disubstituted aryl ring, said substitutions at the para and meta positions, when one substitution is a methoxy group, the other substitution is not a methyl group, a $CH_2$ $(CH_3)_2$ group, an $OC_6H_5$ group, a Cl or a F; and when $R_1$ is H, and Z=$CH_2$, then R is not an unsubstituted phenyl group.

2. The compound of claim 1, wherein Z is S.

3. The compound of claim 2, wherein R is substituted or unsubstituted aryl.

4. The compound of claim 3, wherein R is naphthyl.

5. The compound of claim 3, wherein R is 2,5-dimethyoxyphenyl.

6. A method of inhibiting dihydrofolate reductase and/or thymidylate synthase in a patient comprising:

administering an effective amount of a compound having formula (1):

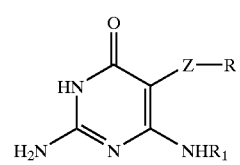

(1)

wherein R is an aryl ring or alkylaryl ring optionally substituted with one or more substituents independently selected from $C_{1-6}$ alkyl groups, $C_{2-6}$ alkenyl groups, $C_{2-6}$ alkynyl groups, $C_{1-6}$ alkoxy groups, halogens, nitro groups, aryl groups, $C_{1-6}$ acyl groups, carboxylic acids, carboxylic esters, hydroxyl groups, mercapto groups, and p-aroyl-L-glutamate;

wherein Z is S, Se, O, NH, $CH_2$; and wherein $R_1$ is H or a straight, branched or cyclic alkyl group having up to about six carbons optionally substituted with one or more halogen, hydroxyl or amine group; but when $R_1$ is H, and Z is $CH_2$, then R is not a 3,4,5 trimethoxyphenyl group; and when $R_1$ is H, Z=$CH_2$ and R is a disubstituted aryl ring, said substitutions at the para and meta positions, when one substitution is a methoxy group, the other substitution is not a methyl group, a $CH_2$ $(CH_3)_2$ group, an $OC_6H_5$ group, a Cl or a F; and when $R_1$ is H, and Z=$CH_2$, then R is not an unsubstituted phenyl group, to said patient.

7. The method of claim 6, wherein said compound is incorporated in a suitable pharmaceutical carrier.

8. The method of claim 7, wherein said carrier is selected from the group consisting of physiologic saline and 5% dextrose for injection.

9. The method of claim 7, including administering said compound by a method selected from the group consisting of parenteral administration, oral administration and topical administration.

10. The method of claim 6, wherein Z is S.

11. The method of claim 10, wherein R is substituted or unsubstituted aryl.

12. The method of claim 11, wherein R is naphthyl.

13. The method of claim 11, wherein R is 2,5-dimethyoxyphenyl.

* * * * *

UNITED STATES PATENT AND TRADEMARK OFFICE
CERTIFICATE OF CORRECTION

PATENT NO. : 6,423,720 B1
DATED : Julu 23, 2002
INVENTOR(S) : Aleem Gangjee

It is certified that error appears in the above-identified patent and that said Letters Patent is hereby corrected as shown below:

Column 1,
Line 22, "cell of." should read -- cell of --.

Column 3,
Line 8, "R," should read -- $R_1$ --.

Column 4,
Lines 40-41, "methylenetetrahydrofolate" should read -- dihydrofolate --.
Line 65, under the column entitled "Compound", line "175", "3-methoyphenyl" should read -- 3-methoxyphenyl --.

Column 6,
Line 35, "abovedescribed" should read -- above-described --.

Column 7,
Line 21, "comparability" should read -- compatability --.
Line 48, "Novel 2 ,4-" should read -- "Novel 2,4- --.

Column 8,
Line 6, start new paragraph with "Anal."

Column 9,
Line 28, "ratio>" should read -- ratio > --.

Signed and Sealed this

First Day of April, 2003

JAMES E. ROGAN
*Director of the United States Patent and Trademark Office*

Disclaimer

6,423,720 — Aleem Gangjee, Allison Park, PA (US), PYRIMIDINE COMPOUNDS AND METHODS FOR MAKING AND USING THE SAME. Patent dated Jul. 23, 2002. Disclaimer filed Nov. 8, 2004, by the Assignee, Duquesne University of the Holy Ghost.

Hereby enters this disclaimer to claims 1-3 and 6-11, of said patent.

*(Official Gazette May 10, 2005)*